(12) United States Patent
Prince et al.

(10) Patent No.: US 11,957,477 B2
(45) Date of Patent: Apr. 16, 2024

(54) ALLERGEN SUPPLY TRAY

(71) Applicants: Ty L. Prince, Knoxville, TN (US); Herman J. Novak, Maryville, TN (US)

(72) Inventors: Ty L. Prince, Knoxville, TN (US); Herman J. Novak, Maryville, TN (US)

( * ) Notice: Subject to any disclaimer, the term of this patent is extended or adjusted under 35 U.S.C. 154(b) by 0 days.

(21) Appl. No.: 18/314,464

(22) Filed: May 9, 2023

(65) Prior Publication Data

US 2023/0270370 A1 Aug. 31, 2023

Related U.S. Application Data (63) Continuation-in-part of application No. 17/658,270, filed on Apr. 7, 2022, which is a continuation-in-part of application No. 17/468,132, filed on Sep. 7, 2021, now Pat. No. 11,369,782, which is a continuation-in-part of application No. 17/402,413, filed on Aug. 13, 2021, now Pat. No. 11,517,249.

(60) Provisional application No. 63/177,515, filed on Apr. 21, 2021, provisional application No. 63/171,995, filed on Apr. 7, 2021, provisional application No. 63/106,793, filed on Oct. 28, 2020.

(51) Int. Cl.
```
A61B 5/00      (2006.01)
A61B 50/00     (2016.01)
A61B 50/30     (2016.01)
A61B 50/33     (2016.01)
A61B 90/00     (2016.01)
```

(52) U.S. Cl.
CPC .............. *A61B 5/411* (2013.01); *A61B 50/33* (2016.02); *A61B 2050/0079* (2016.02); *A61B 2050/3015* (2016.02); *A61B 2090/0808* (2016.02)

(58) Field of Classification Search
CPC . A61B 5/411; A61B 50/33; A61B 2050/0079; A61B 2050/3015; A61B 2090/0808
USPC .......................................................... 600/556
See application file for complete search history.

(56) References Cited

U.S. PATENT DOCUMENTS

| | | | | |
|---|---|---|---|---|
| 5,551,441 | A | * | 9/1996 | Pitesky ................ A61B 17/205 600/556 |
| 5,605,160 | A | * | 2/1997 | Fishman .............. A61B 17/205 600/556 |
| 5,671,753 | A | * | 9/1997 | Pitesky ................ A61B 17/205 600/556 |

(Continued)

*Primary Examiner* — Alex M Valvis
*Assistant Examiner* — Chanel J Jhin
(74) *Attorney, Agent, or Firm* — TechnicalAttorney; Rick Barnes (57) ABSTRACT

An allergen delivery system with a tray and delivery set. The delivery set includes a dispensing well. The dispensing well holds a wettable material to receive an allergen and provide it to a delivery barb that has been received into the dispensing well. A conduit is connected to the dispensing well, to receive the allergen and provide it to the dispensing well. A reservoir is connected to the conduit to receive the allergen and provide it to the conduit. A cap is disposed on the reservoir, with a hole, such that when a finger depresses the cap, the finger covers the hole and the depression creates pressure within the reservoir, which motivates an amount of the allergen to flow out from the reservoir through the conduit and into the dispensing well, to be absorbed by the wettable material, where the allergen is available for delivery to the barbed delivery applicator.

13 Claims, 6 Drawing Sheets

(56) References Cited

U.S. PATENT DOCUMENTS

| | | | | |
|---|---|---|---|---|
| 5,871,452 A * | 2/1999 | Baker | ............... | A61B 5/411 |
| | | | | 600/556 |
| 6,077,229 A * | 6/2000 | Pitesky | ............ | A61B 5/441 |
| | | | | 600/556 |
| 6,206,838 B1 * | 3/2001 | Doll | ............... | A61B 17/205 |
| | | | | 600/556 |
| 2017/0281158 A1 * | 10/2017 | Lear | ............... | A61B 17/076 |

* cited by examiner

ALLERGEN SUPPLY TRAY

PRIORITY

This application claims priority on, and is a CIP of Ser. No. 17/658,270 filed 2022 Apr. 7, which is a CIP of
  Ser. No. 17/468,132 filed 2021 Sep. 7, now U.S. Pat. No. 11,369,782, which is a CIP of
    Ser. No. 17/402,413 filed 2021 Aug. 13, now U.S. Pat. No. 11,517,249, which is a CIP of
      Ser. No. 63/177,515 filed 2021 Apr. 21,
      Ser. No. 63/171,995 filed 2021 Apr. 7, and
      Ser. No. 63/106,793 filed 2020 Oct. 28,
the entirety of the disclosures of which are incorporated herein by reference.

FIELD

This invention relates to the field of allergen testing. More particularly, this invention relates to an allergen supply source tray useful for supplying at least one allergen to at least one allergen delivery device.

INTRODUCTION

Medical professionals in the field of allergy care tend to administer a number of allergens when diagnosing an allergy patient's conditions. The amount of a specific allergen used on a given patient is typically quite small, because a large amount of the allergen is usually not required, and such liquid allergen solutions tend to be extremely expensive. Unfortunately, a relatively larger and costly amount of allergen can be inadvertently wasted during such procedures, even though only a small dose of the allergen is actually administered to the patient.

Many allergen delivery systems create this waste by use of methods and devices that do not allow for a small amount of the allergen to be dispensed, do not adequately prohibit allergen evaporation, or enable the allergen to be easily spilled or cross-contaminated.

What is needed, therefore, is an allergen delivery system by which issues such as these are reduced, at least in part.

SUMMARY

The above and other needs are met by an allergen delivery system having a tray with an allergen delivery set. The allergen delivery set includes an allergen dispensing well that is connected to the tray. The allergen dispensing well holds a wettable material that is adapted to receive a liquid allergen and provide it to a delivery barb that has been received into the allergen dispensing well. An allergen conduit is connected to the allergen dispensing well, and is adapted to receive the liquid allergen and provide it to the allergen dispensing well. An allergen reservoir is connected to the allergen conduit and is adapted to receive the liquid allergen and provide it to the allergen conduit. A pliable cap is removably disposed on the allergen reservoir, with a hole formed therein, such that when a finger depresses the cap, the finger covers the hole and the depression of the cap creates a pressure within the allergen reservoir, which pressure motivates a desired amount of the liquid allergen to flow out from the allergen reservoir through the allergen conduit and into the allergen dispensing well, to be absorbed by the wettable material, where the liquid allergen is then available for delivery to the delivery barb.

In various embodiments according to this aspect of the disclosure, the allergen delivery set includes a barb guide connected to the tray proximate the allergen dispensing well, where the barb guide is adapted to receive and guide the delivery barb into the allergen dispensing well. In some embodiments, the barb guide is releasably attached to the tray.

In some embodiments, at least one of the allergen dispensing well, allergen conduit, and allergen reservoir are integrally molded into the tray. In some embodiments, the allergen delivery system comprises multiple allergen delivery sets.

In some embodiments, a cover covers the allergen delivery system and releasably fits to a circumferential edge of the tray. In some embodiments, the cover is formed of a substantially transparent material. In some embodiments, the cover is magnetically retained to the tray. In some embodiments, the cover includes a retainer for an allergen source bottle. In some embodiments, the retainer is disposed adjacent the allergen delivery set.

In some embodiments, the allergen delivery system includes multiple allergen delivery sets, and the cover includes multiple retainers for multiple different allergen source bottles, wherein each retainer is disposed adjacent an associated one of the allergen delivery sets.

In some embodiments, a given retainer, associated allergen source bottle, and associated allergen delivery set are each marked with a common indicator so that the allergen delivery set is not cross-contaminated with a non-associated one of the allergen source bottles. In some embodiments, the common indicator is at least one of a unique number, color, other indicia, and shape.

According to another aspect of the present disclosure, there is described a method for delivering a liquid allergen to a patient, by dispensing an amount of the liquid allergen into an allergen reservoir. A pliable cap is placed on the allergen reservoir, where the pliable cap has a hole formed therein. The pliable cap is depressed with a finger that is disposed over the hole, thereby motivating a desired amount of the liquid allergen to flow out from the allergen reservoir and into an allergen dispensing well, where the liquid allergen is absorbed by a wettable material. An allergen delivery barb is pressed into the wettable material, so as to receive a dosage of the liquid allergen . The patient is scratched with the allergen delivery barb.

In various embodiments, multiple different liquid allergens are dispensed into multiple associated allergen reservoirs, and are motivated into multiple associated allergen dispensing wells and absorbed by multiple associated wettable materials. Multiple associated allergen delivery barbs are pressed into the multiple associated wettable materials, and the patient is scratched with at least one of the multiple allergen delivery barbs. In some embodiments, the step of pressing the multiple associated allergen delivery barbs into the multiple associated wettable materials is performed substantially simultaneously, and the step of scratching the patent with the multiple allergen delivery barbs is performed substantially simultaneously.

In some embodiments, the liquid allergen is dispensed from a liquid allergen source, where the liquid allergen source and the liquid allergen reservoir are each marked with a common indicator so that the liquid allergen reservoir is not cross-contaminated with a different liquid allergen.

According to yet another aspect of the present disclosure there is described a method for dispensing a liquid allergen to an associated allergen dispensing well without cross-contaminating the liquid allergen. A common indicator is placed on each element of an allergen set, where the elements include a liquid allergen source and a liquid allergen reservoir, where the allergen set is associated with the allergen dispensing well. An amount of the liquid allergen is dispensed from the liquid allergen source bearing the common indicator into the liquid allergen reservoir that also bears the common indicator. A desired amount of the liquid allergen is motivated to flow out from the liquid allergen reservoir and into the associated allergen dispensing well.

In some embodiments, multiple different liquid allergens are dispensed to multiple different associated allergen dispensing wells without cross-contaminating the multiple different liquid allergens, by placing multiple different common indicators on each element of multiple different allergen sets. In some embodiments, the common indicator includes at least one of a shape, a color, an indicium, and a tactile impression.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DESCRIPTION

Figure 1:
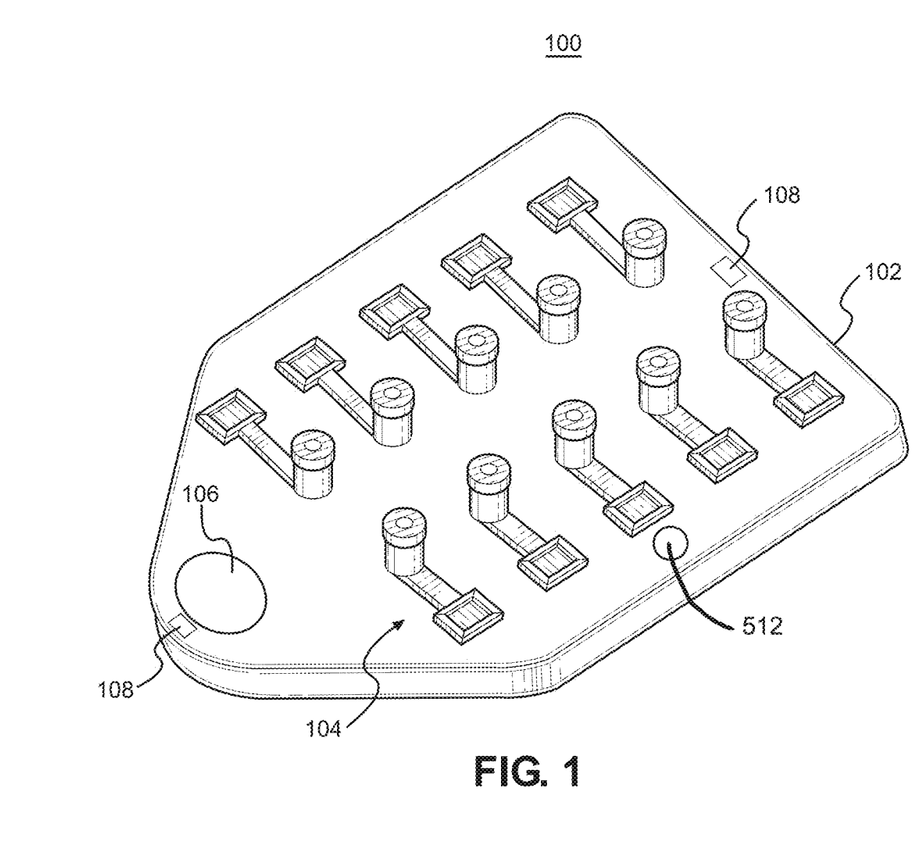
FIG. 1 depicts an allergen delivery system with multiple allergen delivery sets, according to an embodiment of the present disclosure.
Figure 2:
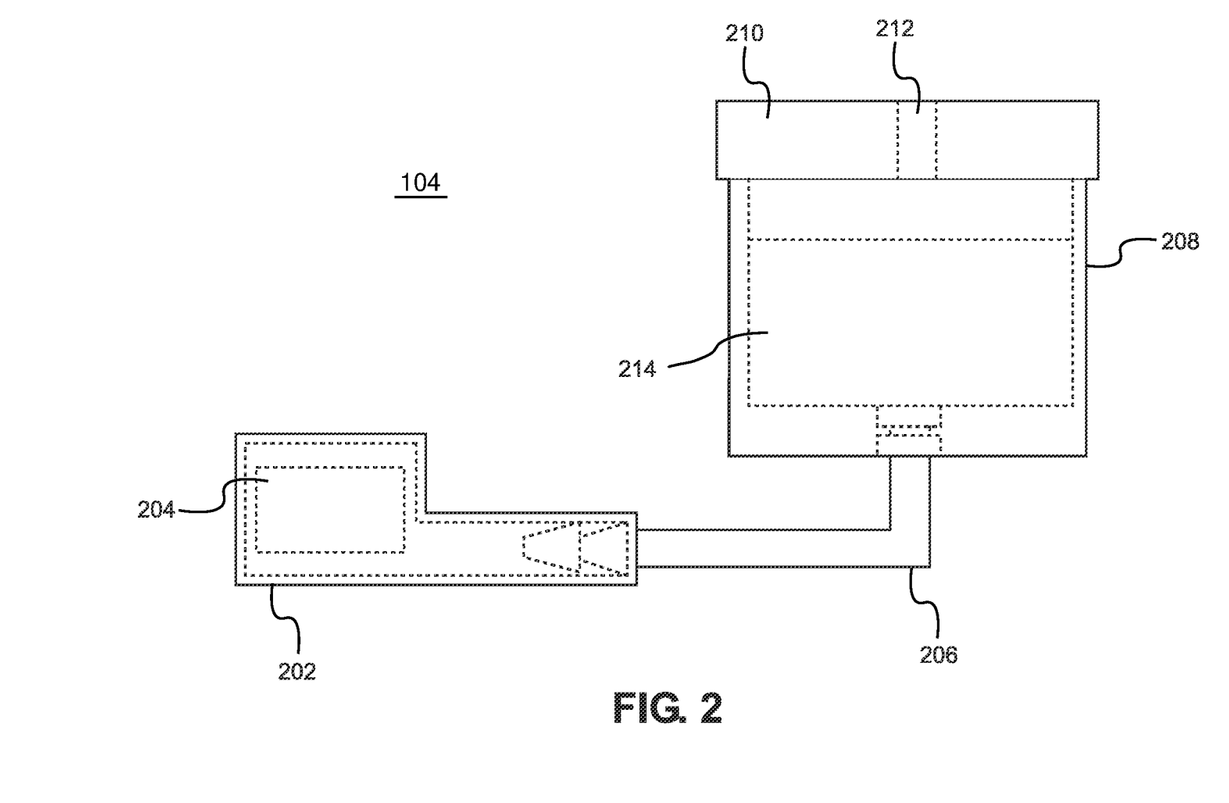
FIG. 2 depicts detail of an allergen delivery set, according to an embodiment of the present disclosure.
Figure 3:
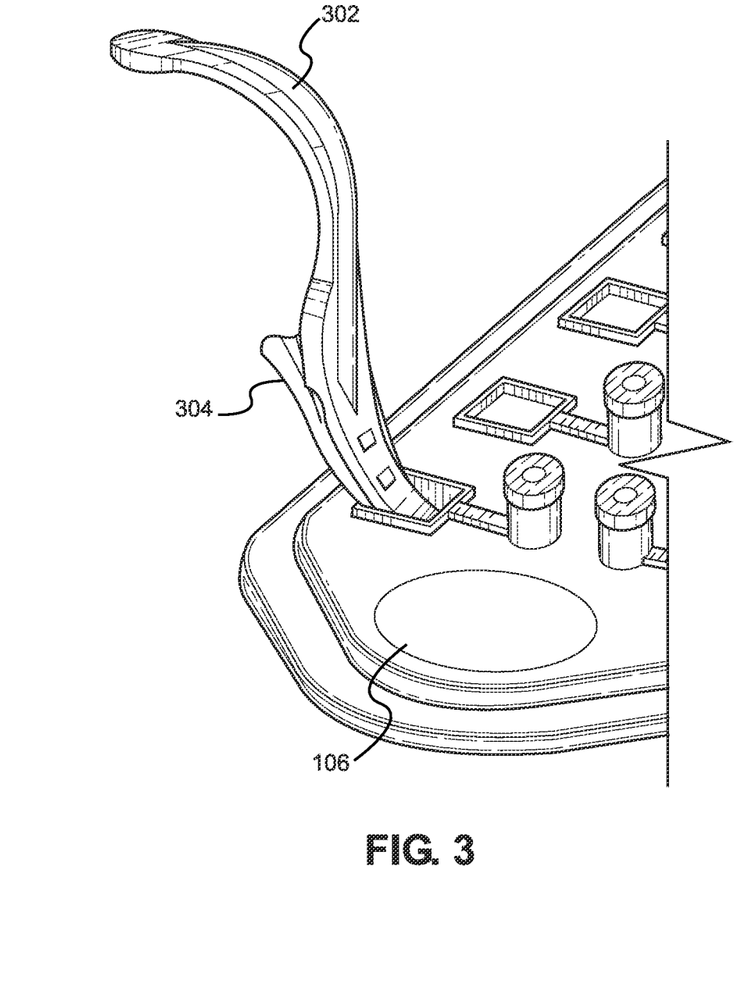
FIG. 3 depicts the use of a single barb applicator with an allergen tray, according to an embodiment of the present disclosure.

With reference now to the drawings, there are depicted all of the claimed elements of the various embodiments, although all claimed embodiments might not be depicted in a single drawing. Thus, it is appreciated that not all embodiments include all of the elements as depicted, and that some embodiments include different combinations of the depicted elements. It is further appreciated that the various elements can all have many different configurations, and are not limited to just the configuration of a given element as depicted. As indicated above, the elements of the drawings as depicted are not to scale, even with respect to one another, and relative size or thickness of one element cannot be determined by the aspect ratios of that element or with reference to any dimension of another element.

Structural Overview

With reference now to FIG. 1, there is depicted an allergen system 100 according to an embodiment of the present disclosure. The allergen system 100 includes a tray 102 having at least one allergen delivery set 104. In the embodiment as depicted, the allergen system 100 includes ten allergen delivery sets, but can have any number of delivery sets 104 on the tray 102, although all of the details of each allergen delivery set 104 have not been included in the figure, so as to not unnecessarily encumber the figure with excessive detail.

Also depicted is a tray indicator 106, which can contain any one or more of a number of different types of identification, such as numbers, letters, colors, and other symbols. In some embodiments, the identification in the tray indicator 106 can be selectively erased so that another identification can be placed therein, and the tray 102 reused for alternate purposes, as described in more detail hereinbelow.

Each delivery set 104 on the tray 102 includes several different elements, as depicted in more detail in FIG. 2. In the embodiment as depicted, the delivery set 104 includes a dispensing well 202 that holds a wettable material 204. The dispensing well 202 is in fluid communication with a conduit 206. The conduit 206 is also in fluid communication with a reservoir 208, having a pliable cap 210, with a hole 212 formed therein.

The reservoir 208 is adapted to contain an amount of a liquid allergen 214. The cap 210 that is place over the reservoir 208, such as after the liquid allergen 214 is placed into the reservoir 208, helps to keep the liquid allergen 214 from evaporating and from being contaminated by other substances that might unintentionally enter the reservoir 208, if the cap 210 were not to be present. The cap 210 also tends to guard against accidentally spilling the liquid allergen 214 that inside the reservoir 208, when the tray 102 is jostled or dropped.

Method of Use

The allergen delivery set is used by filling the allergen reservoir 208 to a desired level, such as half-full, with a liquid allergen 214. The pliable cap 210 is then placed over the top of the reservoir 208. At a point in time when it is desired to dispense an amount of the liquid allergen 214, such as for testing a patient for an allergic reaction to the allergen 214, a finger is placed on the top of the cap 210 at a position that covers the hole 212, and the pliable cap 210 is pushed down, thereby creating a pressure within the reservoir 208, which motivates a desired amount of the liquid allergen 214 to flow through the conduit 206 and into the dispensing well 202, thereby wetting the wettable material 204.

When the desired amount of the liquid allergen 214 has been dispensed into the dispensing well 202, the finger is raised, which removes the pressure from the reservoir 208, and halts the flow of liquid allergen 214 through the conduit 206. Also, as the finger is raised, the hole 212 in the cap 210 is no longer blocked, and ambient air can flow through the hole 212 into the reservoir 208. In this manner, no vacuum is created within the reservoir 208, and the liquid allergen 214 is not drawn back into the reservoir 208 from the conduit 206.

With reference now to FIG. 3, there is depicted a single barbed allergen delivery applicator 302, which is used to deliver an amount of the liquid allergen 214 to a patient. The barbed allergen delivery applicator 302 is used by pressing it into the wettable material 204, which has previously been wet with the liquid allergen 214. This act doses the barbed allergen delivery applicator 302 with an amount of the liquid allergen 214. The barbed allergen delivery applicator 302 is then withdrawn and conveyed to the patient, where it is used to mildly scratch the surface of the patient's skin. This act doses the patient with an amount of the allergen 214. The dosed position on the patient can then be monitored for an allergic reaction.

In some embodiments, a barbed delivery applicator guide 304 is used to help the technician guide the barbed allergen delivery applicator 302 into the dispensing well 202. The barbed delivery applicator guide 304 can also be used to hold the barbed allergen delivery applicator 302 in place in the dispensing well 202, so that the technician does not need to hold the barbed allergen delivery applicator 302 while the barbed allergen delivery applicator 302 resides in the dispensing well 202.

Figure 4:
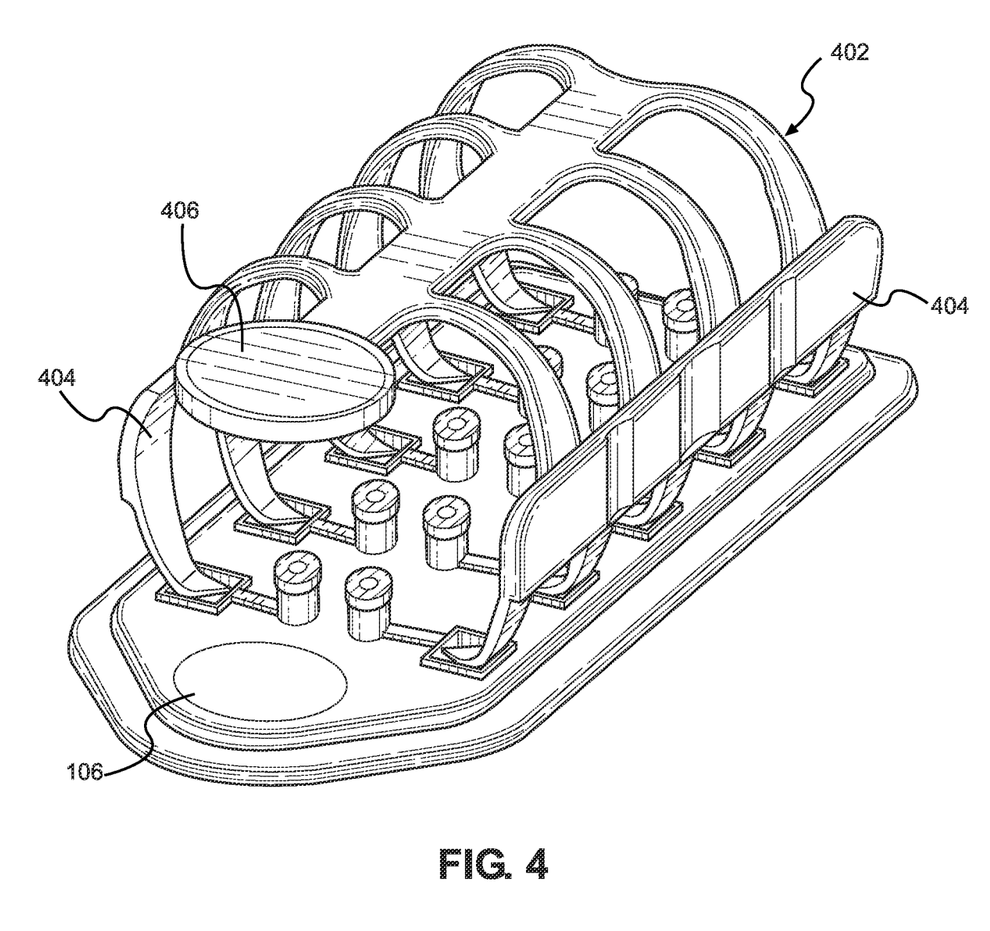
FIG. 4 depicts the use of a multi-barb applicator with an allergen tray, according to an embodiment of the present disclosure.

With reference now to FIG. 4, there is depicted another embodiment according to the present disclosure, where instead of using a single barbed allergen delivery applicator 302, a multi-barbed delivery applicator 402 is used with a tray 102 that has multiple allergen delivery sets 104, where multiple different liquid allergens 214 can be applied to the multi-barbed delivery applicator 402 substantially simultaneously. The multi-barbed delivery applicator 402 can then be pressed against the skin of the patient, and by squeezing the multi-barbed delivery applicator 402 at the two grip points 404, the technician can dose the patient with multiple allergens substantially simultaneously.

The multi-barbed delivery applicator 402 also includes, in some embodiments, a matching indicator 406, which can contain any one or more of a number of different types of identification, such as numbers, letters, colors, and other symbols. In some embodiments, the identification in the matching indicator 406 can be selectively erased so that another identification can be placed therein.

In some embodiments, the identification placed in the matching indicator 406 and the identification placed in the tray indicator 106 are the same, so that it is readily apparent that a matching multi-barbed delivery applicator 402 is associated with a matching tray 106. This can be helpful so that a multi-barbed delivery applicator 402 that has already been used with certain allergens 214 is not placed into a tray 102 with different allergens 214.

In some embodiments both the multi-barbed delivery applicator 402 and the tray 102 and associated elements 104 can be cleaned and sterilized and reused, with different identifications placed into the indicators 106 and 406. In other embodiments, one or both of the multi-barbed delivery applicator 402 and the tray 102 are intended for use with a single patient only, and once used, are thereafter discarded.

Figure 5:
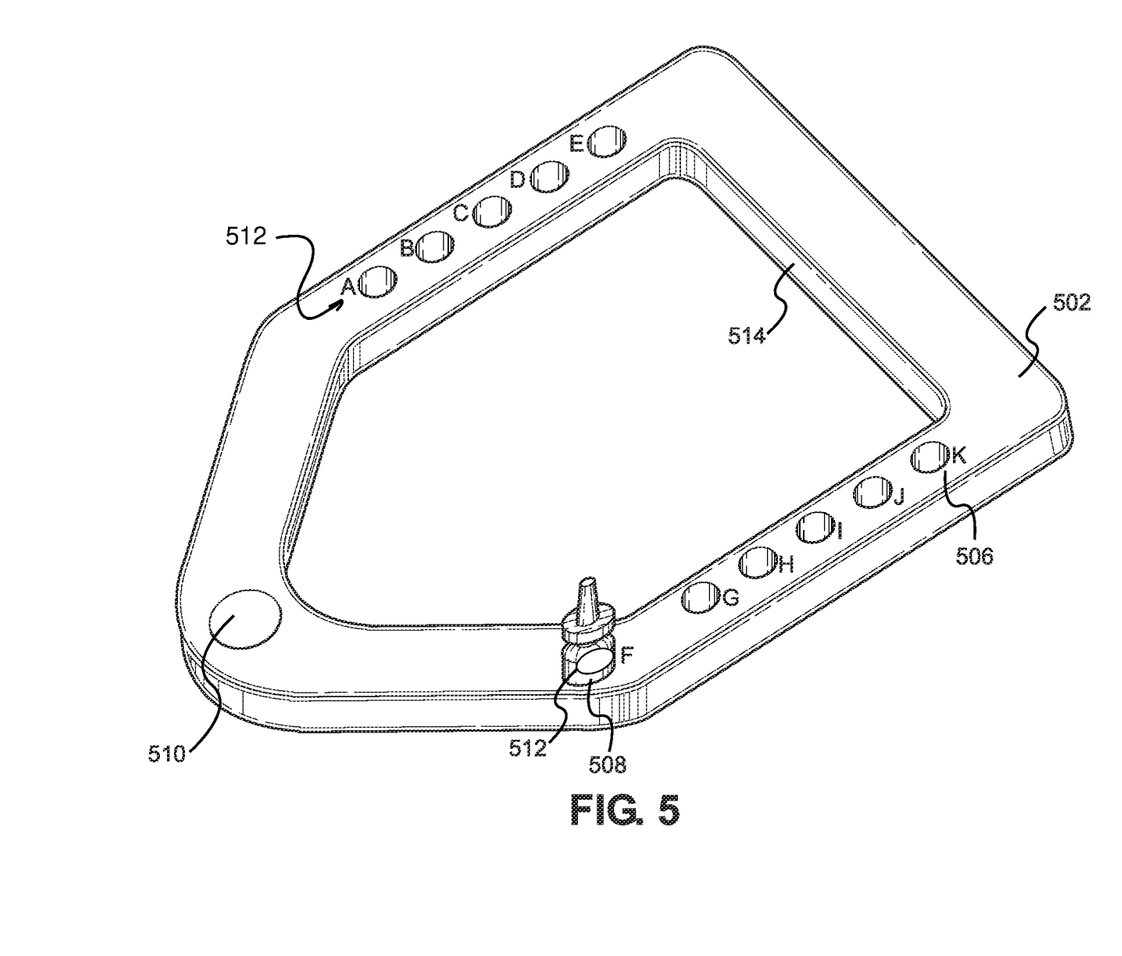
FIG. 5 depicts a source bottle platform, according to an embodiment of the present disclosure.

With reference now to FIG. 5, there is depicted a source bottle platform 502. In some embodiments, the platform 502 includes retainers 506, such as raised rings or cylindrical blind bores, that can releasably retain source bottles 508 of the various allergens 214 that are used with the tray 102.

Some embodiments of the platform 502 also include a platform indicator 510, which can contain any one or more of a number of different types of identification, such as numbers, letters, colors, and other symbols. In some embodiments, the identification in the platform indicator 510 can be selectively erased so that another identification can be placed therein, and the platform 510 reused for alternate purposes.

In some embodiments, the identification placed in the platform indicator 510 is the same as the identification placed in the tray indicator 106 and the matching indicator 406, so that it is readily apparent that a matching multi-barbed delivery applicator 402 is associated with both a matching tray 106 and a matching platform 502. This can be helpful so that a multi-barbed delivery applicator 402 that has already been used with certain allergens 214 is not placed into a tray 102 with different allergens 214, and also so that allergens 214 in the bottles 508 are not used to replenish the reservoirs 208 in a non-associated tray 102.

Figure 6:
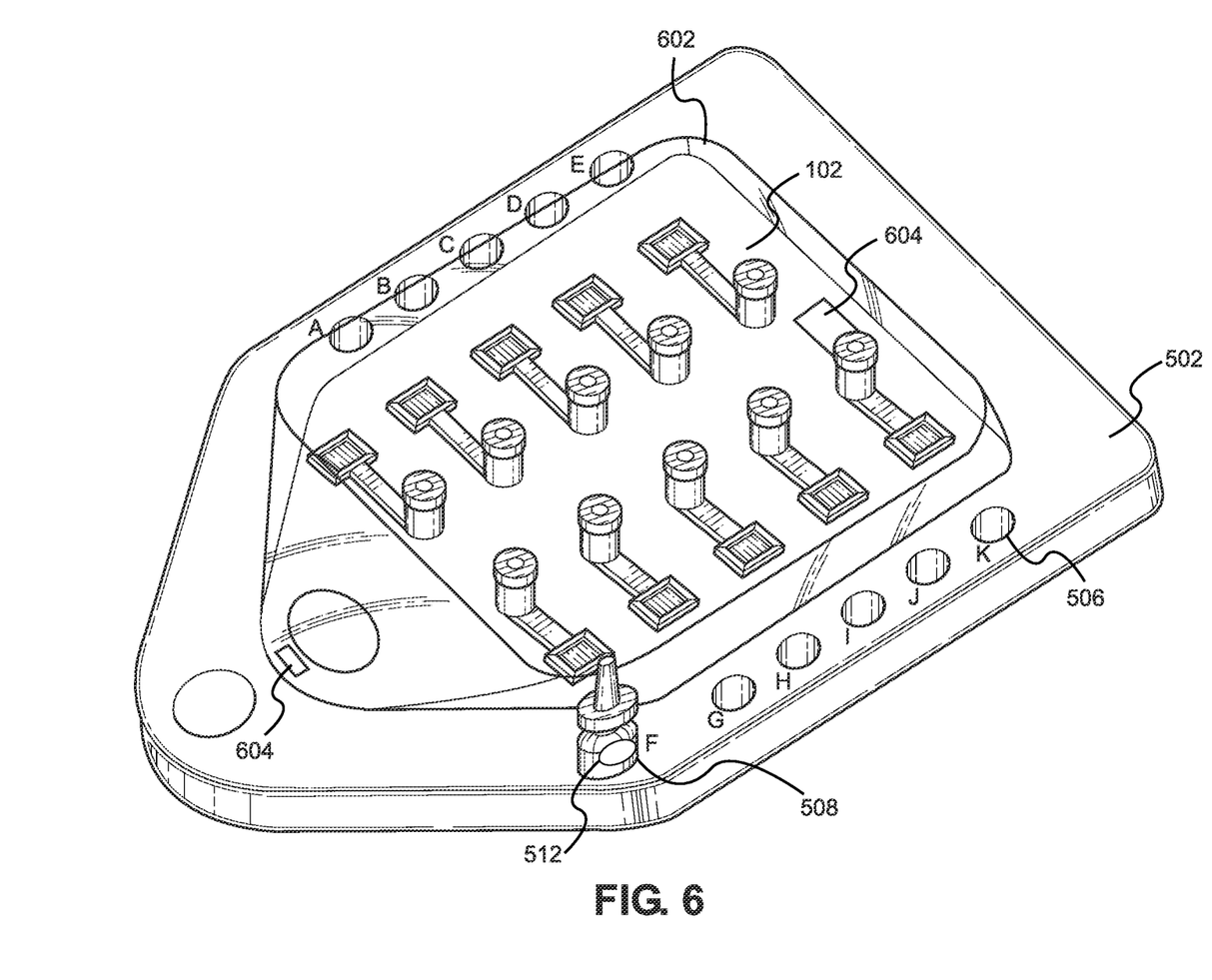
FIG. 6 depicts an allergy delivery tray having a cover with allergen source retainers, according to an embodiment of the present disclosure.

In some embodiments, the platform 502 is press-fit to the tray 102 in such a manner that the platform 502 is held to the tray 102 during normal handling, but can be relatively easily removed from the tray 102, such as by applying some amount of finger-pressure at the interface 514 between the tray 102 and the platform 502, as depicted in FIG. 6.

With further reference to FIG. 6, the tray 102 is disposed within the platform 502, and the tray 102 is covered with a cover 602. In some embodiments the cover 602 is retained to the tray 102 such as with magnets 604, which are attracted to lands 108 on the tray 102. In other embodiments, the tray 102 includes magnets 108 and elements 604 are attracted to the magnets 108. In other embodiments, both the elements 108 and the elements 604 are magnets that engage one another. The cover 602, in some embodiments, protects the liquid allergen 214 that resides within the dispensing well 202 from excessive evaporation, and from airborne contamination, when the allergen system 100 is not in immediate use.

In some embodiments, the retainers 506 are disposed proximate the associated allergen delivery sets 104 that are supplied by the allergen source 508 within the retainer 506. In this manner, it is visually apparent by proximity which liquid allergen 214 is to be used with which allergen delivery set 104, thus reducing the occurrence of cross-contamination of liquid allergen 214 within an allergen delivery set 104.

Further, in some embodiments, a common indicator 512 is placed in proximity to the allergen source bottle 508, source bottle retainer 506, and allergen delivery set 104 that are all used with a common allergen 214. In some embodiments, the common indicator 512 is at least one of a unique number, color, other indicia, and shape. In this manner, the technician can confirm that, for example, the yellow allergen source bottle 508 is placed into the yellow source bottle retainer 506, and the liquid allergen 214 from the yellow source bottle 508 is dispensed into the yellow reservoir 208. In other embodiments, some other type of marking, instead of a color, is placed on each of the allergen source bottle 508, the source bottle retainer 506, and on or near the reservoir 208.

System Construction

In various embodiments, the tray 102 is formed of a plastic, such as by injection molding. The various elements of the delivery set 104 can be separately formed and attached to the tray 102, or can be integrally formed during the fabrication of the tray 102. Different materials can be used to form one or more of the dispensing well 202, conduit 206, and the reservoir 208. The wettable material 204 is, in some embodiments, formed of at least one of natural sponge, open cell foam, and closed cell foam. The pliable cap 210 is, in some embodiments, formed of a material such as latex or a thermoplastic elastomer. In some embodiments, the cover 602 is formed of a substantially clear or transparent plastic. The barbed allergen delivery applicator 302 and multi-barbed delivery applicator 402 are, in various embodiments, formed of at least one of plastic and metal.

As used herein, the phrase "at least one of A, B, and C" means all possible combinations of none or multiple instances of each of A, B, and C, but at least one A, or one B, or one C. For example, and without limitation, the following combinations meet such criteria: A, 2A & B, 2C, A & B & C, 7A & 12 B & 113C. It does not include (0)A & (0)B & (0)C.

The foregoing description of embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An allergen delivery system, comprising:
   a tray, and
   an allergen delivery set, the allergen delivery set comprising,
      an allergen dispensing well connected to the tray, the allergen dispensing well holding a wettable material, the wettable material adapted to receive a liquid allergen within the allergen dispensing well, and provide the liquid allergen to a barbed allergen delivery applicator when the barbed allergen delivery applicator has been received into the allergen dispensing well,
      an allergen conduit connected to the allergen dispensing well, the allergen conduit adapted to receive the liquid allergen and provide the liquid allergen to the allergen dispensing well,
      an allergen reservoir connected to the allergen conduit and adapted to receive the liquid allergen and provide the liquid allergen to the allergen conduit, and
      a pliable cap removably disposed on the allergen reservoir, the cap having a hole formed therein,
         the cap and hole adapted such that when a finger depresses the cap, the finger covers the hole and the depression of the cap creates a pressure within the allergen reservoir, which pressure motivates an amount of the liquid allergen to flow out from the allergen reservoir through the allergen conduit and into the allergen dispensing well to be absorbed by the wettable material, where the liquid allergen is available for delivery to the delivery barb.

2. The allergen delivery system of claim 1, wherein the allergen delivery set further comprises a barbed allergen delivery applicator guide connected to the tray proximate the allergen dispensing well, the barbed allergen delivery applicator guide adapted to receive and guide the barbed allergen delivery applicator into the allergen dispensing well.

3. The allergen delivery system of claim 2, wherein the barbed allergen delivery applicator guide is releasably attached to the tray.

4. The allergen delivery system of claim 1, wherein at least one of the allergen dispensing well and allergen conduit are integrally molded into the tray.

5. The allergen delivery system of claim 1, wherein the allergen delivery system comprises multiple allergen delivery sets, all in association with the tray.

6. The allergen delivery system of claim 1, further including a cover that covers the allergen delivery system and releasably fits to a circumferential edge of the tray.

7. The allergen delivery system of claim 6, wherein the cover includes a retainer for an allergen source bottle.

8. The allergen delivery system of claim 7, wherein the retainer is disposed adjacent the allergen delivery set.

9. The allergen delivery system of claim 7, wherein the allergen delivery system includes multiple allergen delivery sets, and the cover includes multiple retainers for multiple different allergen source bottles, wherein each retainer is disposed adjacent an associated one of the allergen delivery sets.

10. The allergen delivery system of claim 9, wherein a given retainer, and a given allergen source bottle, and the associated one of the allergen delivery sets are each marked with a single common indicator so that the associated one of the allergen delivery sets is not cross-contaminated with another of the allergen source bottles.

11. The allergen delivery system of claim 10, wherein the common indicator is at least one of a unique number, color, other indicia, and shape.

12. The allergen delivery system of claim 6, wherein the cover is formed of a transparent material.

13. The allergen delivery system of claim 6, wherein the cover is magnetically retained to the tray.

* * * * *